(12) United States Patent
Searfoss et al.

(10) Patent No.: US 11,147,963 B2
(45) Date of Patent: Oct. 19, 2021

(54) IMPLANTABLE MEDICAL DEVICES AND METHODS OF MANUFACTURE

(71) Applicant: Oscor Inc., Palm Harbor, FL (US)

(72) Inventors: Timothy Searfoss, New Port Richey, FL (US); Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 0 days.

(21) Appl. No.: 16/003,881

(22) Filed: Jun. 8, 2018

(65) Prior Publication Data

US 2018/0353749 A1 Dec. 13, 2018

Related U.S. Application Data

(60) Provisional application No. 62/517,444, filed on Jun. 9, 2017.

(51) Int. Cl.
*A61N 1/05* (2006.01)

(52) U.S. Cl.
CPC .................. *A61N 1/05* (2013.01)

(58) Field of Classification Search
CPC ........................................ A61N 1/05
See application file for complete search history.

(56) References Cited

U.S. PATENT DOCUMENTS

| | | | | |
|---|---|---|---|---|
| 5,074,313 A * | 12/1991 | Dahl | ............... | A61B 5/042 607/119 |
| 7,130,700 B2 * | 10/2006 | Gardeski | ........... | A61M 25/0021 607/122 |
| 2002/0143377 A1 * | 10/2002 | Wessman | ............... | A61N 1/05 607/116 |
| 2004/0097965 A1 * | 5/2004 | Gardeski | ........... | A61M 25/0021 606/129 |
| 2006/0142652 A1 * | 6/2006 | Keenan | ............... | A61B 18/1492 600/374 |
| 2011/0130817 A1 * | 6/2011 | Chen | ............... | A61N 1/0534 607/116 |
| 2011/0130818 A1 * | 6/2011 | Chen | ............... | A61N 1/0534 607/116 |
| 2015/0021817 A1 * | 1/2015 | Romero | ........... | B29C 45/14065 264/255 |
| 2017/0080215 A1 * | 3/2017 | Osypka | ............... | A61N 1/0551 |

* cited by examiner

*Primary Examiner* — Mallika D Fairchild
(74) *Attorney, Agent, or Firm* — Locke Lord LLP; Scott D. Wofsy; Alicia J. Carroll

(57) ABSTRACT

A method for manufacturing an implantable lead includes forming an elongated lead body core that defines a longitudinal axis. The elongated lead body core has a plurality of axially extending channels that are circumferentially spaced apart from one another around the elongated lead body core. The method also includes positioning an electrode ring around the elongated lead body core and electrical conductors. The method includes positioning a respective electrical conductor in each of the axially extending channels and positioning a dielectric insulator ring around the elongated lead body core and electrical conductors.

9 Claims, 8 Drawing Sheets

IMPLANTABLE MEDICAL DEVICES AND METHODS OF MANUFACTURE

CROSS-REFERENCE TO RELATED APPLICATION

This application claims the benefit of priority to U.S. Provisional Patent Application No. 62/517,444, filed Jun. 9, 2017, which is incorporated by reference herein in its entirety.

BACKGROUND OF THE INVENTION

1. Field of the Invention

The subject disclosure relates to implantable medical devices, and more particularly, to implantable leads that include conductors and contacts.

2. Description of Related Art

Multipolar implantable leads are used for neuro-stimulation to treat certain chronic diseases such as chronic pain, incontinence, Parkinson, depression, and epilepsy. Traditional multipolar implantable leads have multiple electrodes, in most cases a minimum of 4, and in many cases up to 8 or 16 electrodes, which all have to be connected with a conductor of some type but in most cases by a stranded cable (1×19 or 9×9). The leads have very small lead bodies, commonly smaller than 4 French (F) (1.35 mm) in diameter, and have to be isodiametric.

Lead bodies often include a lumen for each conductor to be separately housed. The lead body and areas of dielectric isolation are often manufactured by using a multilumen extrusion. To keep the lead isodiametric, certain areas on the lead body where the actual stimulation electrodes are positioned are getting laser ablated so the electrodes can be stacked up and aligned along the lead body. This process tends to be time consuming and expensive. Specifically, the laser ablation of such small lead body tubing has to be extremely precise as the dimensions of the tubing itself, and the areas to be removed by method of ablation are very small. The precision required with laser ablation can result in a very slow production process.

The conventional techniques have been considered satisfactory for their intended purpose. However, there is an ever present need for improved lead bodies and improved methods of manufacture.

SUMMARY OF THE INVENTION

A method for manufacturing an implantable lead includes forming an elongated lead body core that defines a longitudinal axis. The elongated lead body core has a plurality of axially extending channels that are circumferentially spaced apart from one another around the longitudinal axis of the elongated lead body core. The method includes positioning a respective electrical conductor in each of the axially extending channels. The method includes positioning an electrode ring around the elongated lead body core and at least one of the conductors. The method includes positioning a dielectric insulator ring around the elongated lead body core and adjacent to the electrode ring.

In accordance with some embodiments, the method includes heating the elongated lead body core and the dielectric insulator ring to bond the elongated lead body core and the dielectric insulator ring together.

The method can include positioning additional dielectric insulator rings and electrode rings around the elongated lead body core. It is contemplated that positioning the additional dielectric insulator rings and electrode rings can include positioning them in an axially alternating pattern.

The method can include bonding the electrode ring to at least one of the conductors.

Forming the elongated lead body core can include forming the elongated lead body core by extrusion. The elongated lead body core can include an inner central lumen.

The method can include positioning a dielectric end cap on a distal end of the elongated lead body core and/or a proximal end of the elongated lead body core. It is contemplated that the method can include heating the elongated lead body core and the dielectric end cap to bond the elongated lead body core and dielectric end cap together. The method can include positioning a dielectric sleeve around the elongated lead body core. The dielectric sleeve and/or the dielectric insulator ring can be formed by extrusion.

In accordance with another aspect of the invention, an implantable lead includes an elongated lead body core that defines a longitudinal axis. The elongated lead body core is similar to that formed by the method described above and includes axially extending channels as described above. Respective electrical conductors are in each of the axially extending channels. An electrode ring is positioned around the outer periphery of the elongated lead body core and at least one of the electrical conductors. A dielectric insulator ring is positioned around an outer periphery of the elongated lead body core adjacent to the electrode ring.

Additional dielectric insulator rings and electrode rings can be positioned around the elongated lead body core. It is contemplated that the dielectric insulator rings can be longitudinally spaced apart from one another, and a respective one of the electrode rings can be positioned between two of the longitudinally adjacent spaced apart dielectric insulator rings. The electrode ring can be bonded to at least one of the conductors. A dielectric end cap can be positioned on a distal end and/or a proximal end of the elongated lead body core. A dielectric sleeve can be positioned around the elongated lead body core.

These and other features of the subject invention and the manner in which it is manufactured, assembled and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION OF THE PREFERRED EMBODIMENTS

Figure 1:
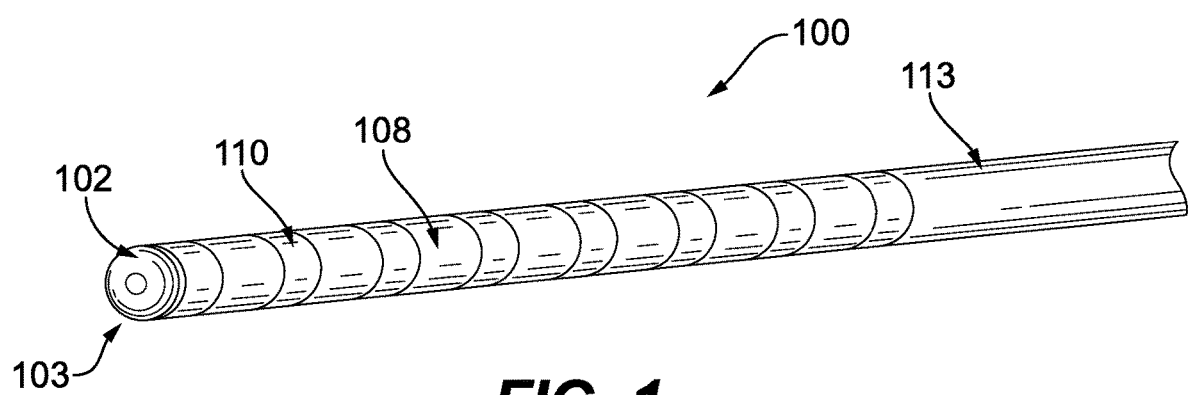
FIG. 1 is a schematic perspective view of a distal end portion of an implantable medical device, showing dielectric insulator rings positioned between axially adjacent spaced apart electrode rings.
Figure 12:
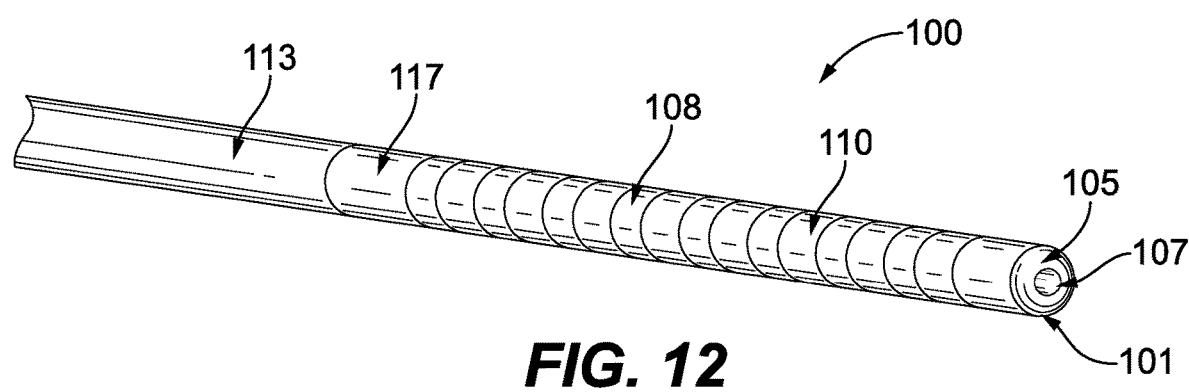
FIG. 12 is a schematic perspective view of a proximal end portion of the implantable medical device of FIG. 1, showing a similar construction to that of the distal end.

Referring now to the drawings wherein like reference numerals identify similar structural features and/or elements of the subject matter disclosed herein, there is illustrated in FIG. 1 a distal end 103 of an implantable lead 100. A proximal end 101 of the implantable lead 100 is shown in FIG. 12. Proximal end 101 has a configuration similar to distal end 103 and can be inserted into an active medical stimulator device, or the like, as disclosed for example in commonly assigned U.S. Patent Application Publication 2012/0253445, the disclosure of which is herein incorporated by reference in its entirety. Embodiments described herein address the issues with the precision required in manufacturing implantable leads. Embodiments of the disclosure provide a manufacturing process that avoids the manufacturing complexities associated with laser ablating small lead body tubing, resulting in an implantable lead that can be manufactured in less time and for reduced cost.

Figure 2:
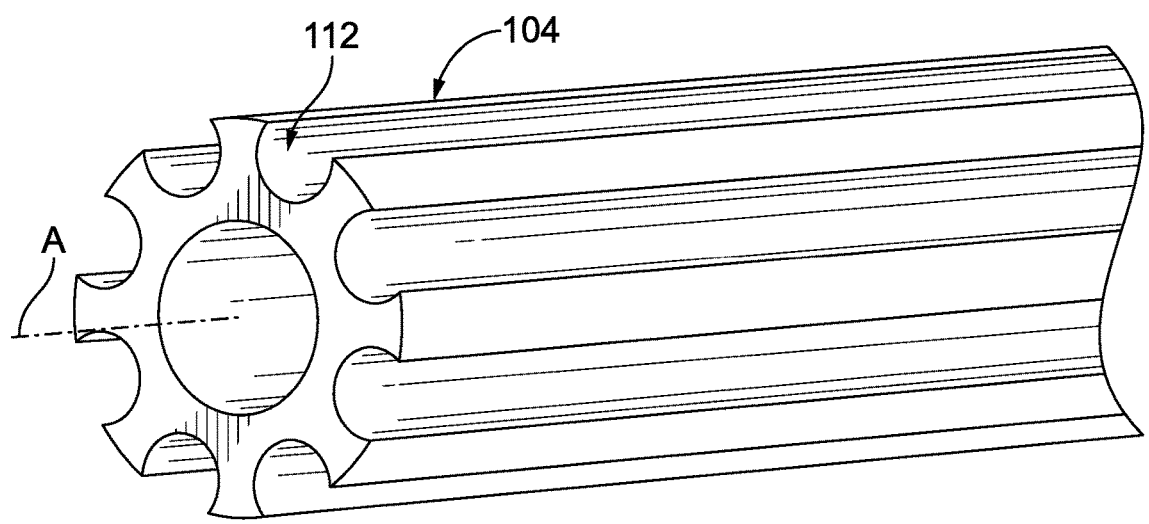
FIG. 2 is a schematic perspective view of a distal end portion of an elongated lead body core of the implantable medical device of FIG. 1, showing axially extending channels and an axially extending lumen.
Figure 3:
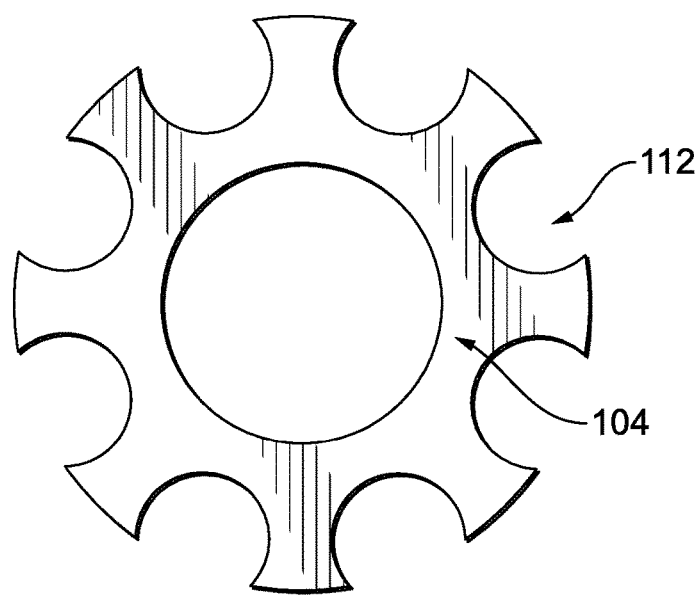
FIG. 3 is a schematic plan view of the distal end of the elongated lead body core of FIG. 2.
Figure 13:
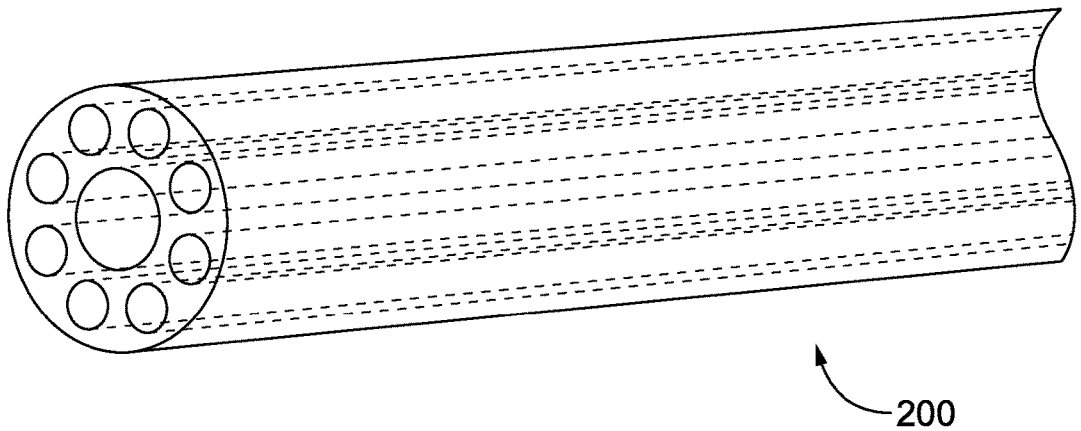
FIG. 13 is a schematic perspective view of an extruded lead body core with enclosed lumen for each conductor to be separately housed.
Figure 14:
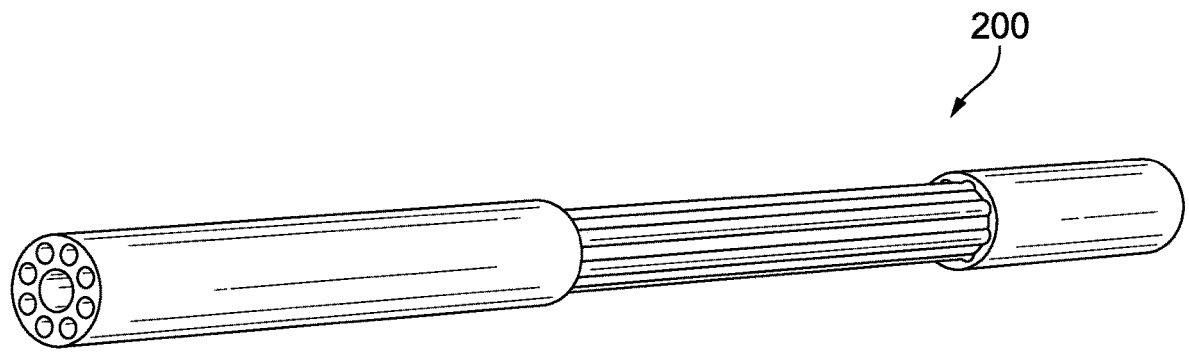
FIG. 14 is a schematic perspective view of the extruded lead body core of FIG. 13, with a portion of the outer diameter laser ablated so the electrodes can be stacked up and aligned along the lead body.

As shown in FIG. 1, distal end 103 of implantable lead 100 includes dielectric insulator rings 108 positioned between axially adjacent spaced apart electrode rings 110. An end cap 102 covers distal tip of implantable lead 100. Implantable lead 100 also includes a dielectric insulator sleeve 113. With reference now to FIGS. 2-3, implantable lead 100 is formed with an elongated lead body core 104 that defines a longitudinal axis A. FIGS. 2-3 show a distal end of elongated lead body core 104. Those skilled in the art will readily appreciate that a proximal end portion of elongated lead body core 104 is similar to that of distal end 103. Elongated lead body core 104 has a plurality of axially extending channels 112 that are circumferentially spaced apart from one another around longitudinal axis A of elongated lead body core 104 and an inner central lumen extending therethrough. Lead body core 104 and its channels 112 are formed through extrusion, e.g. plastic extrusion. FIG. 2 shows lead body core 104 after extrusion. After extrusion, axially extending channels 112 are open, e.g. not enclosed by additional dielectric material like a body 200 of FIG. 13. The extrusion of the very small profile of lead body core 104 can be performed with extrusion tooling with a 2 to 4 draw down ratio. Due to this ratio, it is contemplated that the extrusion tooling can be manufactured by laser micro-machining. By forming lead body core 104 through extrusion, instead of forming the entire body including an outer diameter shell covering the channels through extrusion (as shown in prior art FIGS. 13 and 14), the need to laser ablate the outer diameter (as shown in FIG. 14) to make room for electrode rings 110 is avoided with lead body core 104. This reduces manufacturing time and cost and makes large scale production of implantable lead 100 easier.

Figure 4:
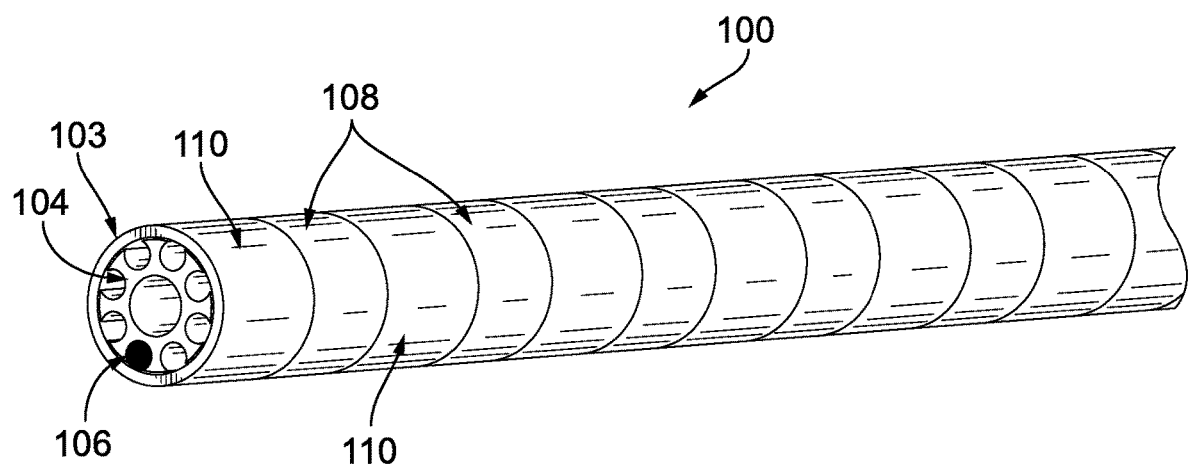
FIG. 4 is a schematic perspective view of the distal end portion of the implantable medical device of FIG. 1 with the end cap removed, showing an electrical conductor positioned within one of the axially extending channels of the elongated lead body core.

With reference now to FIG. 4, conductor 106 is positioned in respective axially extending channel 112. Axially alternating dielectric insulator rings 108 and electrode rings 110 are positioned around elongated lead body core 104 and electrical conductors 106. Any suitable number of dielectric insulator rings 108 and electrode rings 110 can be positioned around elongated lead body core 104.

Figure 5:
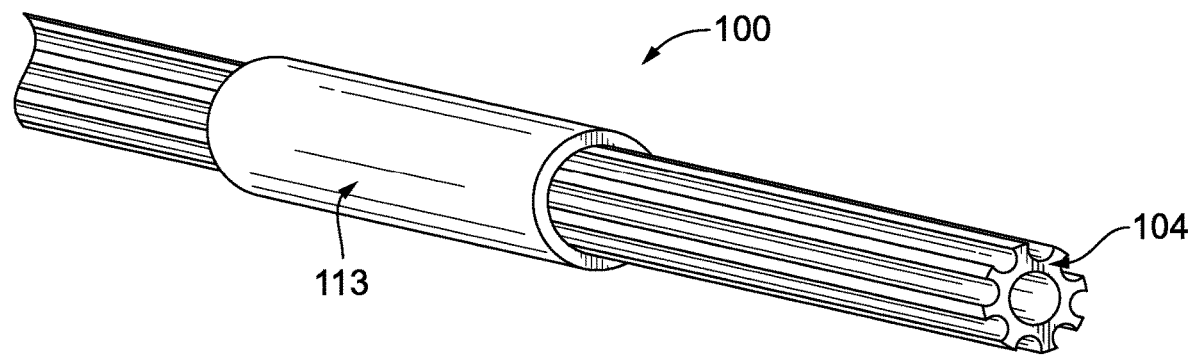
FIG. 5 is a schematic perspective view of the distal end of the elongated lead body core of FIG. 2, showing a dielectric insulator sleeve positioned over the elongated lead body core.
Figure 6:
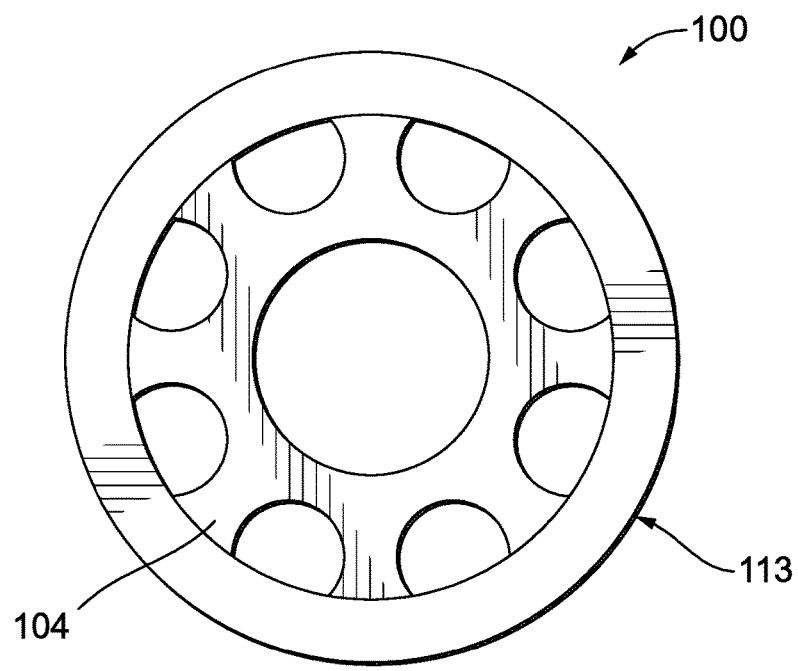
FIG. 6 is schematic a cross-sectional view of the distal end of the elongated lead body core of FIG. 2 and the dielectric insulator sleeve.
Figure 7:
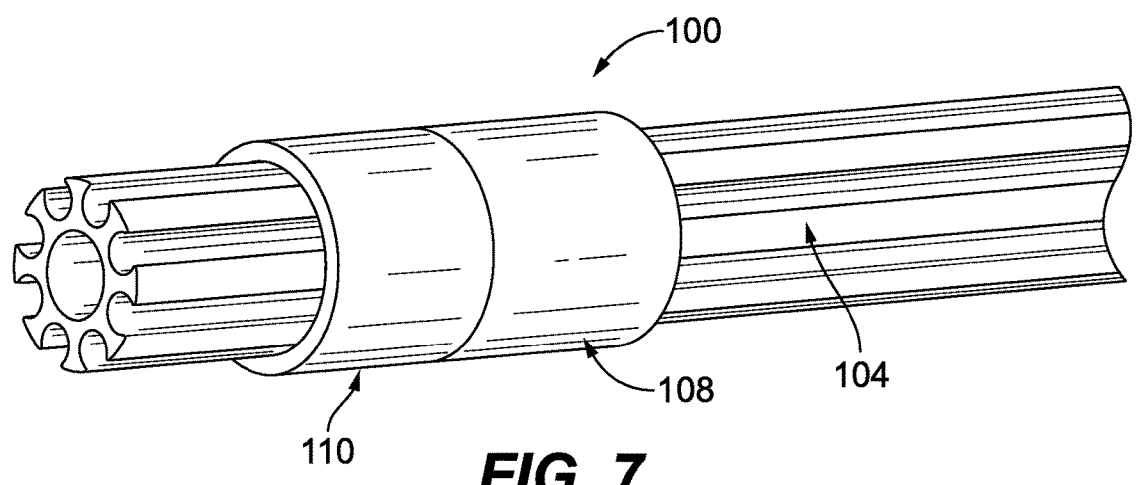
FIG. 7 is a schematic perspective view of a portion of the implantable medical device of FIG. 1, with a dielectric insulator ring and an electrode ring sliding over the outer periphery of the elongated lead body core as they are being positioned.

As shown in FIGS. 5-6, a dielectric insulator sleeve 113 is slid around the outer periphery of elongated lead body core 104, before electrical conductors 106 are positioned. Sleeve 113 encloses a portion of axially extending channels 112. With reference now to FIG. 7, one of dielectric insulator rings 108 and one of electrode rings 110 are slid around the outer periphery of elongated lead body core 104 as they are being positioned.

Figure 8:
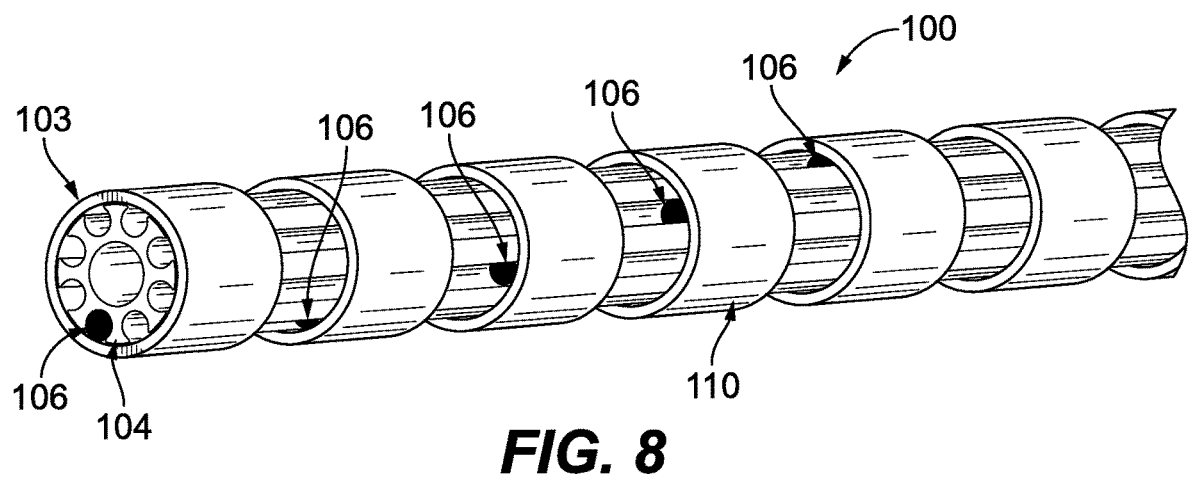
FIG. 8 is a schematic perspective view of a portion of the implantable medical device of FIG. 1, showing a series of axially spaced apart electrode rings positioned around the elongated lead body core and multiple conductors.

As shown in FIG. 8, a series of axially spaced apart electrode rings 110 are positioned around elongated lead body core 104 and multiple conductors 106. Conductors 106 are shown with shaded ends to distinguish between conductors 106 and their respective longitudinal channels 112. The gaps between electrode rings 110 are where dielectric insulator rings 108 are positioned. Dielectric insulator rings 108 are not shown for clarity.

Figure 9:
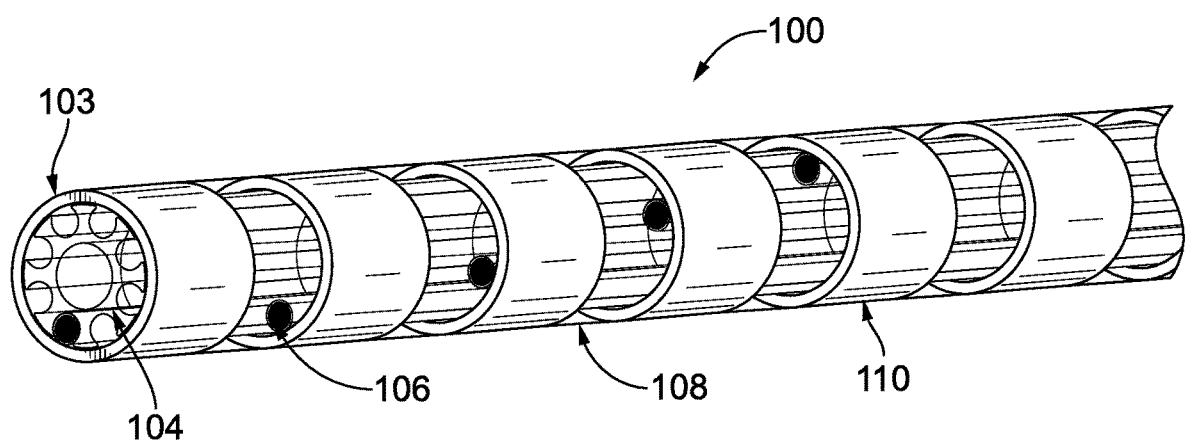
FIG. 9 is a schematic perspective view of a portion of the implantable medical device of FIG. 1, showing the dielectric insulator rings translucently so that the conductors are visible.

FIG. 9 shows implantable lead 100 of FIG. 1 without end cap 102. Elongated lead body core 104 and dielectric insulator rings 108 are shown translucently so that conductors 106 can be seen. Those having skill in the art will readily appreciate that elongated lead body core 104 and dielectric insulator ring 108 can be opaque, translucent or transparent.

Figure 10A:
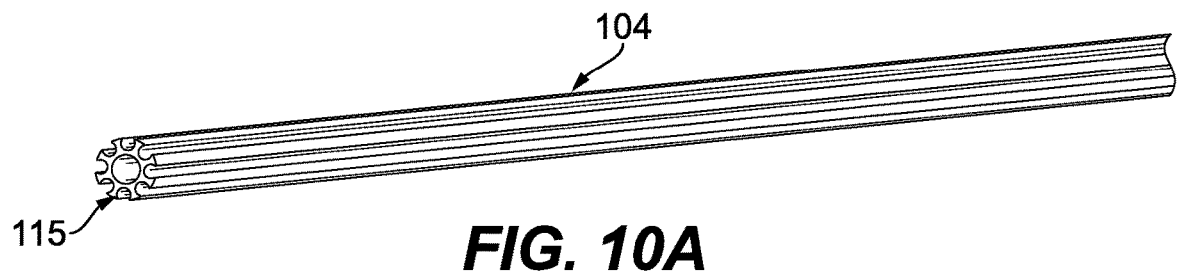
FIG. 10A is a schematic perspective view of a distal end portion of the elongated lead body core of the implantable medical device of FIG. 1, after extrusion.
Figure 10B:
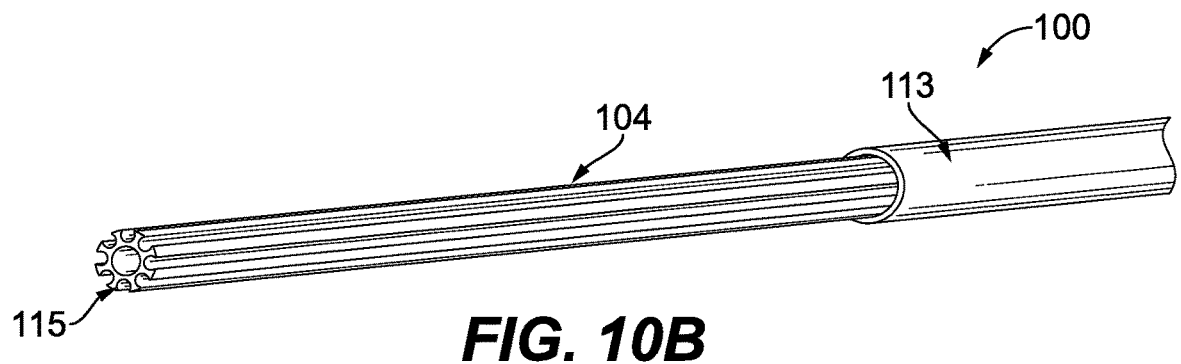
FIG. 10B is a schematic perspective view of a distal end portion of the elongated lead body core of the implantable medical device of FIG. 1, showing a dielectric insulator sleeve slid around the elongated lead body core.
Figure 10C:
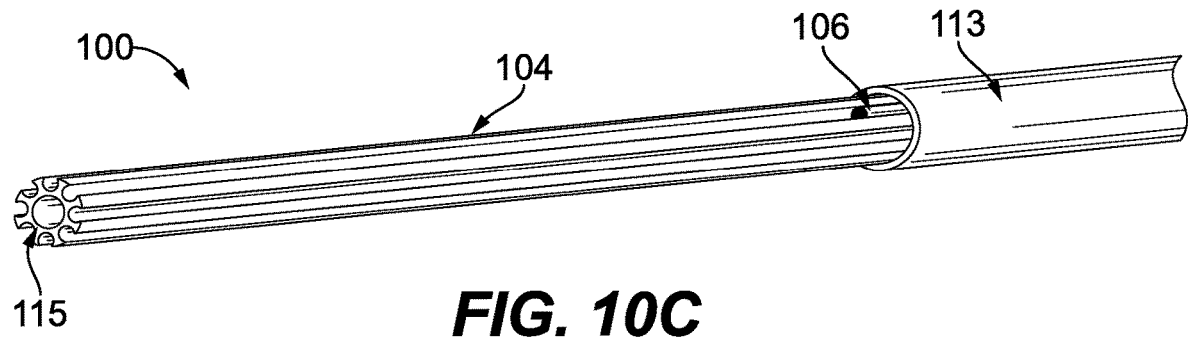
FIG. 10C is a schematic perspective view of a distal end portion of an elongated lead body core of the implantable medical device of FIG. 1, showing a respective electrical conductor being positioned in an axially extending channel of the elongated lead body core.
Figure 10D:
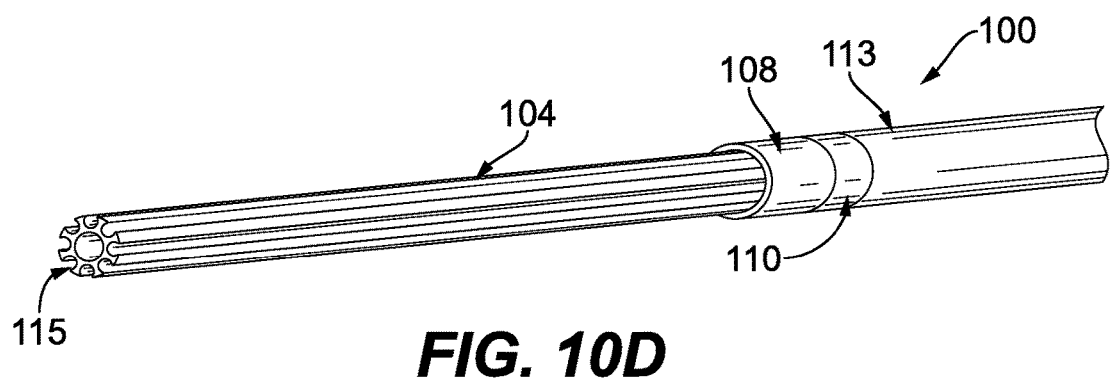
FIG. 10D is a schematic perspective view of a distal end portion of an elongated lead body core of the implantable medical device of FIG. 1, showing an electrode ring and dielectric insulator ring being stacked around the elongated lead body core.
Figure 10E:
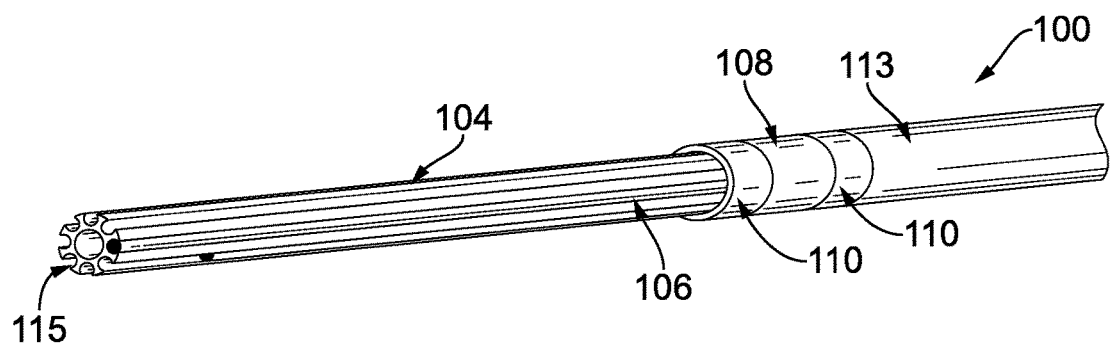
FIG. 10E is a schematic perspective view of a distal end portion of an elongated lead body core of the implantable medical device of FIG. 1, showing two electrode rings and dielectric insulator ring stacked around the elongated lead body core.

A method for manufacturing implantable lead 100 is shown in FIGS. 10A-10E. An embodiment of the method includes extruding elongated lead body core 104, shown in FIG. 10A, where elongated lead body core 104 includes axially extending channels 112 that are open, e.g. not enclosed. It is contemplated that elongated lead body core 104 can be molded, additively manufactured, or the like. The method includes positioning a dielectric insulator sleeve 113 around elongated lead body core 104, e.g. by sliding dielectric insulator sleeve 113 around elongated lead body core 104, shown in FIG. 10B. Respective electrical conductors 106 are then positioned in each of axially extending channels 112, one of which is shown in FIG. 10C. Embodiments of the method include positioning electrode rings 110 and dielectric insulator rings 108 around elongated lead body core 104, e.g. by sliding electrode rings 110 and dielectric insulator rings 108 around elongated lead body core 104, as shown in FIGS. 10D-10E. Sleeve 113 and rings 108 can similarly be extruded, molded, additively manufactured, or the like.

Figure 11:
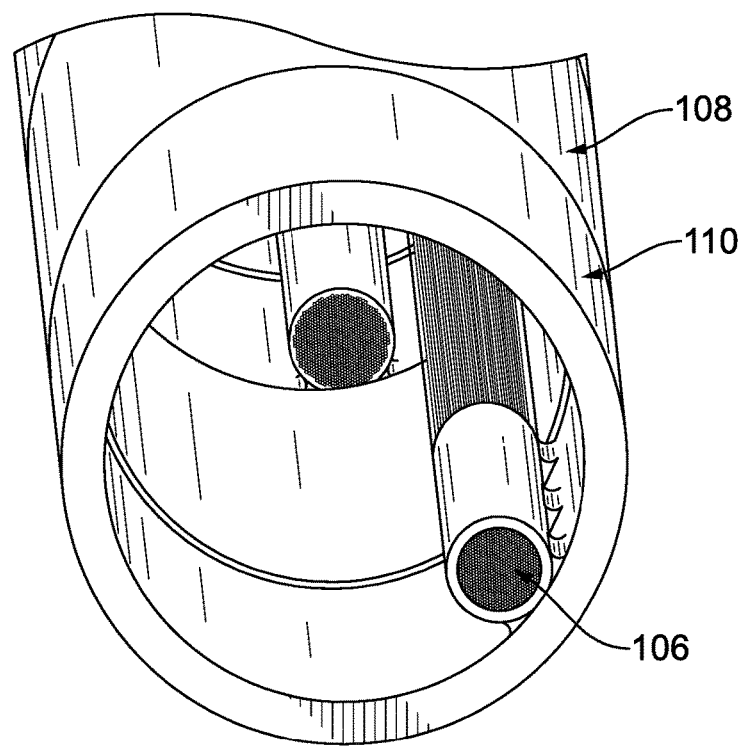
FIG. 11 is a schematic perspective view of a portion of the implantable medical device of FIG. 1 from the distal end, showing one of conductors being bonded to a respective electrode ring.

As shown in FIG. 11, after positioning one of electrode rings 110 embodiments of the method include bonding that electrode ring 110 to a respective conductor 106 by laser welding. Elongated lead body core 104 is not shown in FIG. 11 for sake of clarity. Laser welding can be repeated after the positioning of each electrode ring 100. Those skilled in the art will readily appreciate that while dielectric insulator rings 108 and electrode rings 110 are shown stacked in an alternating sequence, they can be stacked in a variety of suitable sequences. After insulator rings 108 and electrode rings 110 are stacked and cover body core 104 almost to its distal end 115, embodiments of the method include positioning dielectric end cap 102 on the distal end of the implantable lead 100, shown in FIG. 1. In accordance with some embodiments, heat, e.g. reflow, is applied after assembly of dielectric insulator rings 108, electrode rings 110 and end cap 102 onto lead body core 104.

With reference now to FIG. 12, proximal end 101 of lead 100 has a similar construction and is manufactured in a similar manner, e.g. by using the method described above with reference to FIGS. 10A-10E. Elongated lead body core 104 and conductors 106 (not shown, as they are covered over by dielectric insulator sleeve 113, electrode rings 110 and dielectric insulator rings 108) extend from a portion of lead 100 near distal end 103 to a portion of lead 100 near proximal end 101. The portion of insulator sleeve 113 that is shown in FIG. 12 is a proximal end portion of sleeve 113 shown in FIG. 1.

With continued reference to FIG. 12, one additional "anchor" electrode 117 is positioned between the proximal end of insulator sleeve 113 and one of dielectric insulator rings 108. Anchor electrode 117 can be positioned on core 104 by sliding anchor electrode 117 around elongated lead body core 104. Anchor electrode 117 is not electrically connected. In use, the active medical stimulator device (not shown) has a set screw that anchors into anchor electrode 117 to prevent proximal end 101 from separating from the active medical stimulator device. A second end cap 105 is positioned on proximal end 101 of lead 100. Second end cap 105 is different from end cap 102 in that it has a center opening 107 the same diameter as the inner central lumen of core 104 to facilitate the introduction of a stylet (not shown) that introduces implantable lead 100 into a patient and is then removed from lead 100 after implant. Once fully assembled, the entire implantable lead assembly 100 is reflowed (heated along length) to bond all components together, becoming one piece.

After re-flow, assembly 100 is run between two grinding wheels and centerless ground along its full length to polish an outer diameter to a smooth uniform outer diameter. While the method for manufacture is described herein in the context of implantable lead 100 it is contemplated that the method described herein can be applied to other embodiments of implantable leads, or the like.

The methods and systems of the present disclosure, as described above and shown in the drawings, provide for implantable medical devices, such as heart leads, neuro-sensing and neuro-stimulation devices, and intervention catheters and devices, manufactured in a manner that reduces manufacturing time and expense. While the apparatus and methods of the subject disclosure have been shown and described with reference to preferred embodiments, those skilled in the art will readily appreciate that changes and/or modifications may be made thereto without departing from the scope of the subject disclosure.

What is claimed is:
1. A method for manufacturing an implantable lead comprising:
a) forming an elongated lead body core that defines a longitudinal axis, wherein the elongated lead body core has a plurality of axially extending channels that are circumferentially spaced apart from one another around the longitudinal axis of the elongated lead body core;
b) positioning a respective electrical conductor in each of the axially extending channels;
c) positioning an electrode ring around the elongated lead body core and at least one of the electrical conductors;
d) positioning a dielectric insulator ring around the elongated lead body core and adjacent to the electrode ring;
e) positioning a dielectric end cap on a distal end of the elongated lead body core;
f) heating the elongated lead body core, the dielectric end cap and the dielectric insulator ring to bond the elongated lead body core, the dielectric end cap and the dielectric insulator ring together to form the implantable lead; and
g) grinding an outer diameter of the implantable lead, including the dielectric end cap, to a smooth uniform outer diameter.

2. A method as recited in claim 1, further comprising positioning additional dielectric insulator rings and electrode rings around the elongated lead body core.

3. A method as recited in claim 2, wherein positioning the additional dielectric insulator rings and electrode rings includes positioning them in an axially alternating pattern.

4. A method as recited in claim 1, further comprising bonding the electrode ring to at least one of the conductors.

5. A method as recited in claim 1, wherein forming the elongated lead body core includes forming the elongated lead body core by extrusion.

6. A method as recited in claim 1, wherein the elongated lead body core includes an inner central lumen.

7. A method as recited in claim 1, further comprising positioning a second dielectric end cap on a proximal end of the elongated lead body core.

8. A method as recited in claim 1, further comprising positioning a dielectric sleeve around the elongated lead body core.

9. A method as recited in claim 8, further comprising forming the at least one of the dielectric sleeve or the dielectric insulator ring by extrusion.

\* \* \* \* \*